(12) United States Patent
Okabe

(10) Patent No.: US 8,048,011 B2
(45) Date of Patent: Nov. 1, 2011

(54) ULTRASONIC-TREATMENT HANDPIECE WITH HEAT/VIBRATION BLOCKING STRUCTURE AND ULTRASONIC TREATMENT APPARATUS USING THE HANDPIECE

(75) Inventor: Hiroshi Okabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 1936 days.

(21) Appl. No.: 10/967,364

(22) Filed: Oct. 18, 2004

(65) Prior Publication Data

US 2005/0085803 A1   Apr. 21, 2005

(30) Foreign Application Priority Data

Oct. 17, 2003   (JP) .................................. 2003-357931

(51) Int. Cl.
*A61B 17/32*   (2006.01)
(52) U.S. Cl. ...................................... 601/169
(58) Field of Classification Search ............ 606/27, 606/37, 48, 169, 40, 170; 604/22, 113, 114
See application file for complete search history.

(56) References Cited

U.S. PATENT DOCUMENTS

| | | | | |
|---|---|---|---|---|
| 5,026,387 | A | * | 6/1991 | Thomas ......................... 606/169 |
| 5,059,210 | A | * | 10/1991 | Clark et al. .................... 606/169 |
| 2006/0142672 | A1 | * | 6/2006 | Keast et al. ........................ 601/2 |

FOREIGN PATENT DOCUMENTS

| | | |
|---|---|---|
| JP | 2002-253568 | 9/2002 |
| WO | WO/93/05715 | 4/1993 |

* cited by examiner

*Primary Examiner* — Elizabeth Houston
*Assistant Examiner* — Thomas McEvoy
(74) *Attorney, Agent, or Firm* — Scully, Scott, Murphy & Presser, P.C.

(57) ABSTRACT

An ultrasonic handpiece for use in operations comprises an oscillation source and a casing unit. The oscillation source has an ultrasonic transducer formed by plural piezoelectric layers layered one on another to form a substantially rod shape having both ends in an axial direction. A radially expanded flange is attached one end of the ultrasonic transducer. The casing unit has a cylindrical casing formed to contain the oscillation source therein, formed to have a blocking layer formed to have a predetermined length in, the axial direction, and positioned to cover both the flange and at least a first piezoelectric layer of the ultrasonic transducer in the axial direction. The casing unit also has a holder holding the oscillation source within the casing using the flange. The blocking layer is in charge of blocking (reducing or preventing) vibration and heat from being transmitted to the outer surface of the casing.

24 Claims, 10 Drawing Sheets

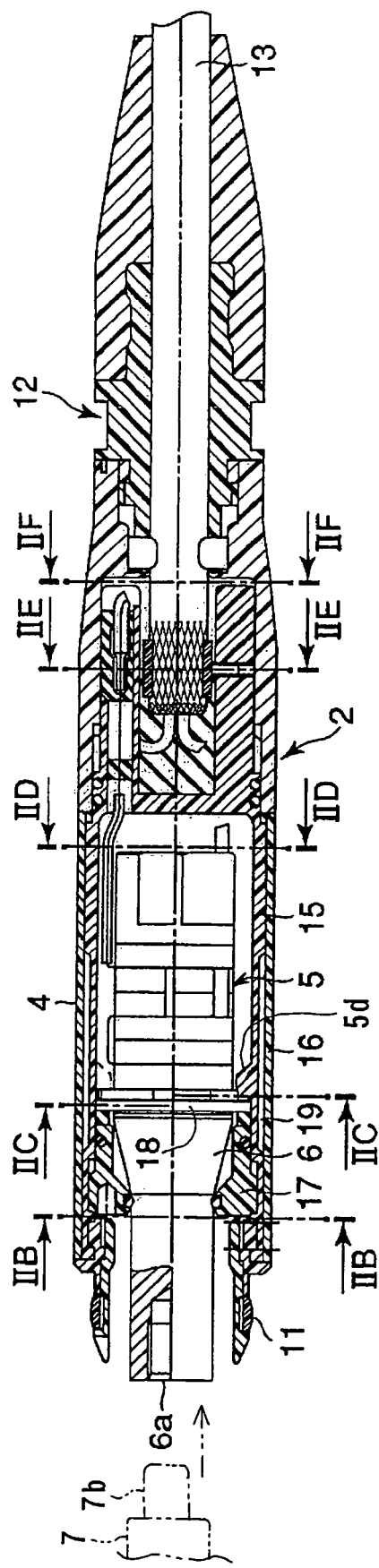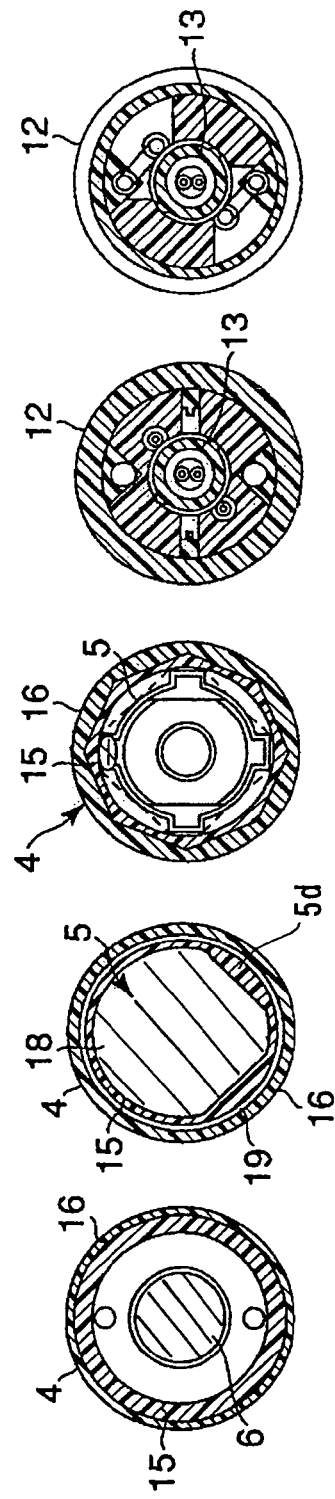
FIG. 2A
FIG. 2B  FIG. 2C  FIG. 2D  FIG. 2E  FIG. 2F

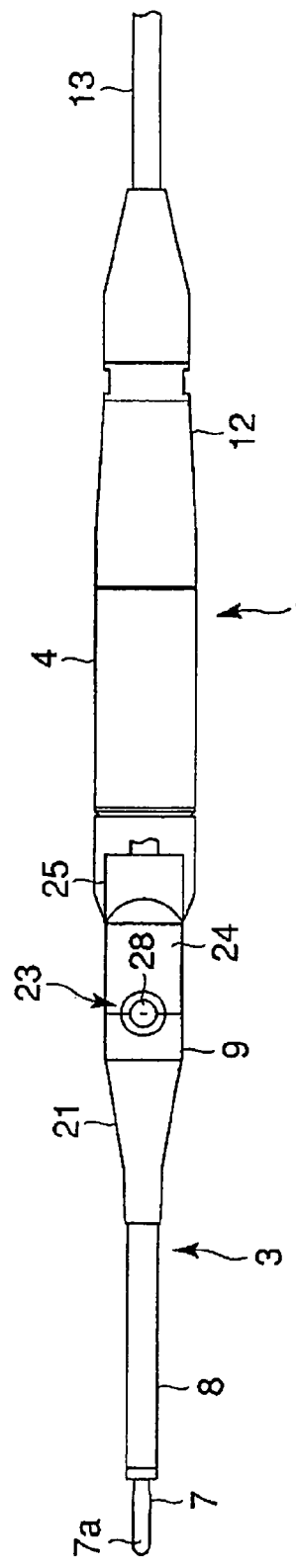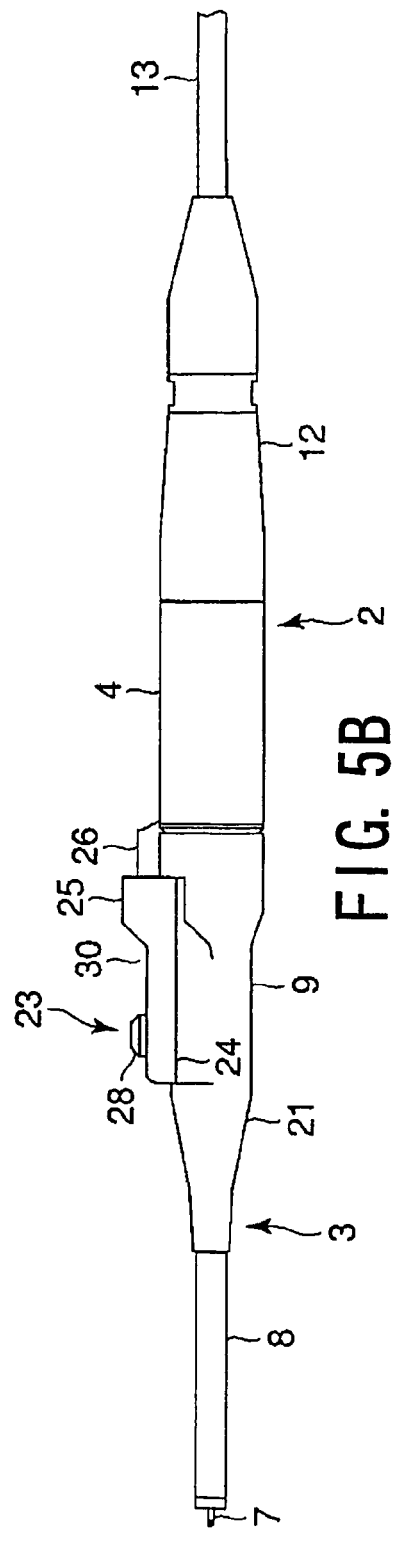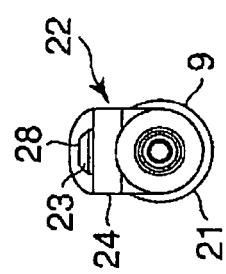
FIG. 5A
FIG. 5B
FIG. 5C

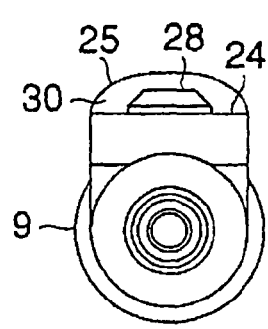
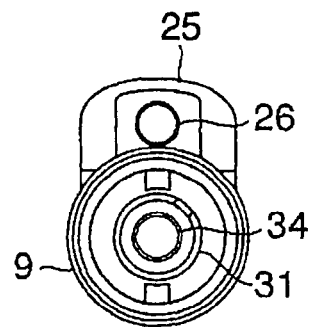
FIG. 7A    FIG. 7B
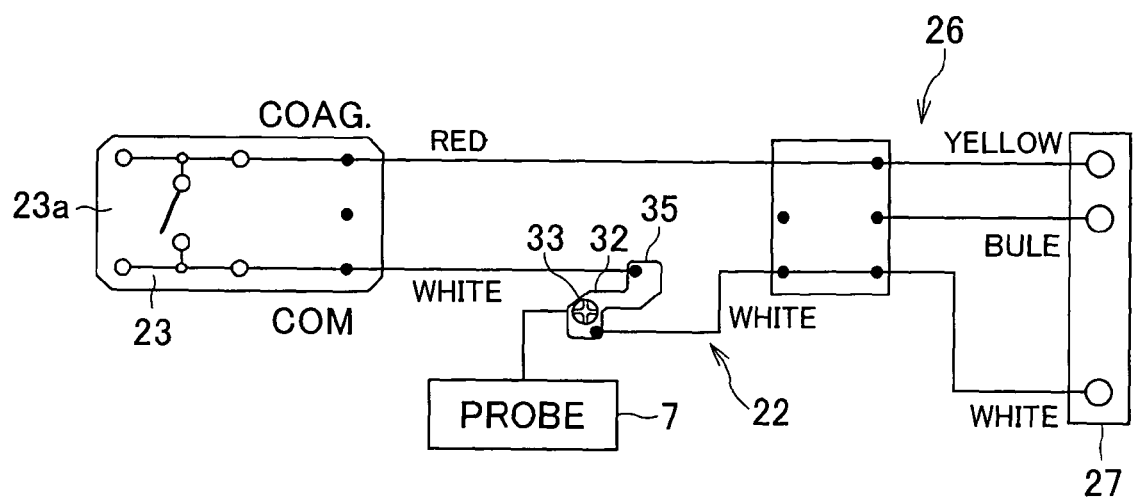
FIG. 8

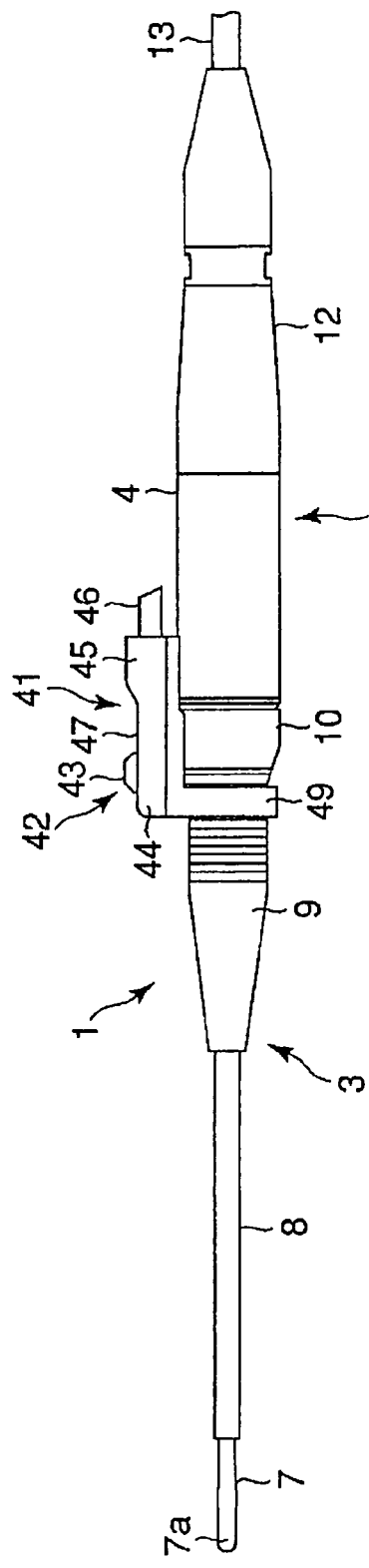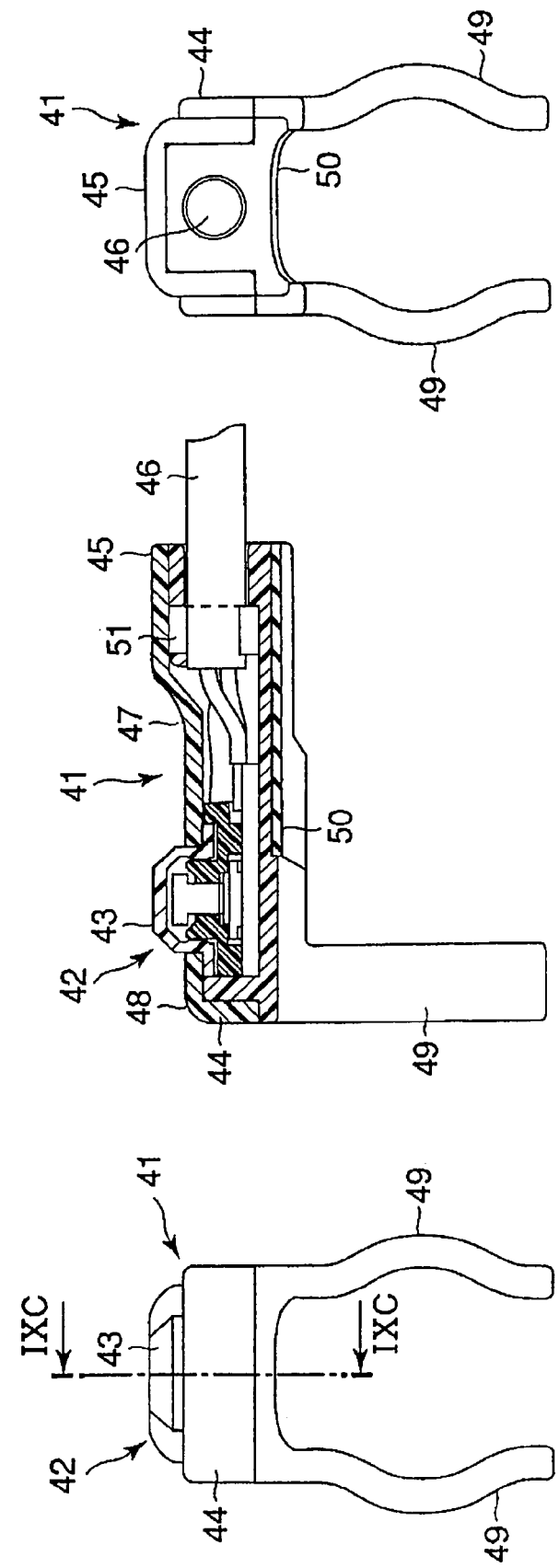
FIG. 9A
FIG. 9B
FIG. 9C
FIG. 9D

ULTRASONIC-TREATMENT HANDPIECE WITH HEAT/VIBRATION BLOCKING STRUCTURE AND ULTRASONIC TREATMENT APPARATUS USING THE HANDPIECE

CROSS REFERENCES TO RELATED APPLICATIONS

The present application relates to and incorporates by reference Japanese Patent application No. 2003-357931 filed on Oct. 17, 2003.

BACKGROUND OF THE INVENTION

1. Technical Field

The present invention relates to a handpiece for treating anatomy utilizing ultrasonic vibration generated by an ultrasonic transducer and an ultrasonic treatment apparatus provided with the handpiece, and in particular, to the handpiece with a structure preventing transmission of heat and vibration caused when the ultrasonic transducer is driven to continuously generate ultrasound vibration and the ultrasonic treatment apparatus provided with the handpiece with the heat/vibration blocking structure.

2. Related Art

Ultrasonic treatment apparatuses have been known as devices which use ultrasonic vibration to conduct surgical operations including treatments, such as emulsification, incision, ablation, and coagulation, of anatomy of an object to be treated. In general, the ultrasonic treatment apparatus is provided with a main unit in charge of the drive and control necessary for the ultrasonic treatments, a cable connected to the main unit, and an operation apparatus with a handpiece connected to the cable for the treatments. This handpiece is provided with an ultrasonic transducer generating ultrasonic vibration, a thin and long probe receiving the ultrasonic vibration to transmit the vibration to the distal end thereof, and a casing covering the ultrasonic transducer as well as the outer surface of part of the probe other than the distal treatment device thereof. The ultrasonic transducer is incorporated within a gripping portion of the handpiece griped by an operator.

During use of the ultrasonic treatment apparatus, the vibration caused by the ultrasonic transducer is transmitted to the distal treatment device of the probe through its thin and long body. With the distal treatment device vibrating, the probe is operated to make the distal treatment device come in contact with anatomy to be treated, so that the anatomy is subject to the foregoing ultrasonic treatments.

The conventional handpiece of this kind is proposed by, for example, International publication No. WO 93/05715 (publication 1) and Japanese Patent Laid-open publication No. 2002-253568 (publication 2).

Of these, the publication 1 provides an apparatus that employs the above handpiece, in which there are formed a probe and an ultrasonic transducer through which an aspiration channel is formed. In this handpiece, there is also provided a casing with elongated outer and inner shells formed therein. Between the outer and inner shells, an irrigation channel is formed to supply cleaning fluid. In this apparatus, the cleaning fluid is supplied from the irrigation channel between the outer and inner shells to the tip of the probe, and the cleaning fluid is aspirated through an aspiration hole formed at an axial center part of the probe tip to the aspiration channel formed to axially pass the probe and ultrasonic transducer at the center thereat.

On the other hand, the publication 2 proposes a handpiece, wherein a casing incorporating therein an ultrasonic transducer and providing a gripping portion is placed to have an intermediate layer formed between an innermost layer and an outermost layer within the transducer cover. Both the innermost and outermost layers are formed of electrically insulative material and the intermediate layer is formed of material of which hygroscopicity is different from that of the outermost and innermost layers.

During use of the above ultrasonic treatment apparatus, the ultrasonic transducer located within the gripping portion held by an operator is driven to oscillate continuously. In this operation, the ultrasonic transducer is subjected to the continuous oscillation, resulting in that a fixing portion to fixedly hold a flange of the transducer in the casing of the handpiece will suffer from heat generated from the fixing portion as well as the transducer. This heat generation is an issue to be solved, because, during the use, the heat generated at the fixing portion holding the flange of the transducer in the gripping portion will be transmitted to the surface of the gripping portion, thereby raising the temperature of the gripping portion up considerably high. In addition, when the ultrasonic transducer is driven in a continuous oscillation mode, such vibration will also be transmitted to the gripping portion. The thus-transmitted vibration may reduce a skin friction coefficient of the gripping portion, so that the gripping portion becomes easier to slip from the hands. Thus the vibration on the griping portion may affect operations for the treatments performed under the probe.

Moreover, the configurations proposed by the foregoing publications 1 and 2 have other difficulties.

Within the casing of the handpiece employed by the apparatus proposed by the publication 1, the irrigation channel to supply cleaning fluid is placed between the outer and inner shells. Thus, the irrigation channel may provide a function to prevent the heat and vibration from being transmitted to the gripping portion. However, in this configuration, there should be formed the hole through the axial center part of the probe and ultrasonic transducer. The cleaning fluid also should be fed from the irritation channel between the outer and inner shells to the probe tip, and then the cleaning fluid should be aspirated through the aspiration hole formed at the axial center part of the probe tip to the aspiration channel formed at the center of the probe and ultrasonic transducer. Hence there is a problem that the handpiece itself becomes large in its size, particularly, in the radial direction thereof.

Meanwhile, the apparatus disclosed by the publication 2 should have the casing that not only covers the ultrasonic transducer but also becomes the gripping portion, in which the intermediate layer is formed between the outermost and innermost layers in the cover. However, since the intermediate layer is made of a material whose hygroscopicity is different from that of the outermost and innermost layers, a situation is inevitable where, during the use, the heat caused at the fixing portion fixedly supporting the ultrasonic transducer in the gripping portion finally reaches the outer surface of the gripping portion. Hence the gripping portion of the handpiece cannot be prevented from becoming heated in an effective manner, which is another difficulty that the conventional structure suffers.

SUMMARY OF THE INVENTION

The present invention has been made with due consideration to the foregoing various difficulties, and an object of the present invention is to provide a handpiece for use in ultrasonic treatments in surgical operations and an ultrasonic treatment apparatus, in which heat and vibration caused by an ultrasonic transducer under a continuous oscillation are prevented or suppressed from being transmitted to a gripping portion of the handpiece in a steadier manner, thus providing a high heat/vibration blocking (reducing or preventing) effect and the entire gripping portion is still avoidable from becoming larger in size, particularly, in the radial direction.

The "blocking layer" and "heat/vibration blocking layer" according to the present invention are defined as a layer that is capable of "blocking" (i.e., "reducing" or "preventing") the transmission of the heat and vibration. In other words, each of the "blocking layer" and "heat/vibration blocking layer" according to the present invention includes a condition where the almost complete block of transmission of the heat and vibration as well as a further condition where the transmission of the heat and vibration is reduced, even to a certain degree. Though being expressed as the "layer," the thickness of the "layer" is not limited to a particular one, and the layer should be construed as a construction of having both a heat blocking effect and a vibration blocking effect and of having a smaller dimension in the radial direction of the handpiece than those in both the axial and circumferential directions of the handpiece.

In order to accomplish the foregoing object, as one aspect of the present invention, there is provided an ultrasonic handpiece for use in operations. This handpiece comprises an oscillation source equipped with an ultrasonic transducer generating ultrasonic vibration; and a casing unit equipped with a casing having a blocking layer blocking transmission of heat and oscillation and a holder holding the oscillation source within the casing.

In general, in cases where the ultrasonic transducer in the oscillation source is driven in, for example, a continuous oscillation mode to cause the oscillation source to output ultrasonic vibration continuously, heat is generated, together with vibration, from the oscillation source. Normally, as the output of the vibration becomes higher, an amount of the heat rises as well. Further, since the holder holding the oscillation source is made to contact the casing and vibration results from the mutually contacted portion between the casing and the oscillation source is transformed into frictional heat, an amount of heat generated from this mutually contacted portion is forced to rise.

However, using the casing unit according to the present invention, the transmission of the above heat and vibration is surely blocked (i.e., reduced or prevented) by the blocking layer. Thus the heat and vibration transmitted to the outer surface of the casing unit, which forms part of the handpiece and is gripped by an operator, can be blocked (i.e., reduced or prevented). It is also possible to avoid the vibration on the casing unit from affecting operations for the treatments. In addition, the blocking layer is positioned to face a particular range from which the heat and vibration are caused mainly. This positioning avoids the handpiece from expanding unnecessarily, thereby making the handpiece (that is, the casing unit) more compact.

As another aspect of the present invention, there is provided an ultrasonic handpiece for use in operations. This handpiece comprises an oscillation source and a casing unit. Of these, the oscillation source is equipped with an ultrasonic transducer formed by a plurality of piezoelectric layers each generating ultrasonic vibration and being layered one on another to form a substantially rod shape having both ends in a layered direction serving as an axial direction, a radially expanded flange being attached on a circumferential surface of one of the ends of the ultrasonic transducer. The casing unit is equipped with a casing formed into an approximately cylindrical shape to contain the oscillation source therein, formed to have a heat/vibration blocking layer formed to have a predetermined length in the axial direction, formed to compass along a circumferential direction of the oscillation source, and positioned to cover both the flange and at least a first piezoelectric layer of the ultrasonic transducer in the axial direction, and a holder holding the oscillation source within the casing using the flange.

In this handpiece, as described above, the vibration and heat caused in association with driving the oscillation source is blocked (i.e., reduced or prevented) by the blocking layer formed within the wall portion of the casing unit. The casing unit is also avoided from expanding in size in its radial direction. Further, the handpiece is easy to use. In addition, the blocking layer is located to include an axial range including the flange as well as at least the first piezoelectric layer of the ultrasonic transducer. More concretely, it can be said that the blocking layer surely encloses an axial range from which a large quantity of vibration and heat is generated. The vibration and heat can therefore be blocked (reduced or prevented) at higher efficiency.

In the above configuration of the handpiece, it is preferred that the oscillation source includes an amplitude amplification element coupled with the ultrasonic transducer at a one axial end of the transducer, the one axial end facing the flange, and formed to amplify amplitude of the ultrasonic vibration generated by the transducer. The amplitude amplification element is for example a horn (or horn assembly). When this horn is used for amplifying the amplitudes, the transmission of the heat and vibration can be reduced or prevented without fail, because the blocking layer faces an axial range including the flange of the transducer.

Another preferred example is that the blocking layer has a first end extending toward the ultrasonic transducer in the axial direction, a position of the first end of the blocking layer being positioned to reach the last piezoelectric layer of the ultrasonic transducer in the axial direction, and/or a second end extending toward the amplitude amplification element in the axial direction, a position of the second end of the blocking layer being positioned to reach a predetermined position over the flange in the axial direction. This way of locating the blocking layer makes it possible that heat and vibration caused by continuously driving the oscillation source can be reduced or prevented steadily from being transmitted to the outer surface of the casing unit.

It is also preferred that the casing is provided with a substantially cylindrical inner casing enclosing an outer circumferential surface of the oscillation source and a substantially cylindrical outer casing enclosing an outer circumferential surface of the inner casing, wherein the blocking layer is formed between the inner and outer casings. Hence the blocking layer can be formed easily, whereby, unlike the conventional, there is no necessity for employing a complicated handpiece structure in which fluid is circulated.

Preferably, the above casing can be structured such that the blocking layer is for instance an air-tight air layer and the blocking layer is lower in heat conductivity than the inner and outer casings. Using this structure, a blocking layer with heat-blocking (insulating) effect and vibration-blocking (insulating) effect can be produced more easily.

Moreover, the present invention provides an ultrasonic treatment apparatus that has the similar operations and advantages to the foregoing and a casing unit for an ultrasonic-treatment handpiece.

The other operations and advantageous technical features will be made clear from the descriptions of the following embodiments and the accompanying drawings.

BRIEF DESCRIPTION OF THE DRAWINGS

In the accompanying drawings:

FIG. 2A is an axial section view showing the internal structure in an axial direction (long direction or longitudinal direction) of the transducer unit shown in FIG. 1B;

FIGS. 2B to 2F are sections showing IIB-IIB, IIC-IIC, IID-IID, IIE-IIE and IIF-IIF lines in FIG. 2A, respectively;

FIG. 5A is a plane view showing an outer appearance of a main part (focusing on a handpiece) of an operation apparatus adopted by an ultrasonic treatment apparatus according to a second embodiment of the present invention;

FIG. 5B is a side view of the handpiece shown in FIG. 5A;

FIG. 5C is a frontal view of the handpiece shown in FIG. 5A;

FIG. 7A is a frontal view of the handpiece in the second embodiment;

FIG. 7B is a rear view of the sheath unit in the second embodiment;

FIG. 8 outlines an electrical diagram given to the handpiece adopted by the ultrasonic treatment apparatus according to the second embodiment;

FIG. 9A is a plane view showing an outer appearance of a main part (focusing on a handpiece) of an operation apparatus adopted by an ultrasonic treatment apparatus according to a third embodiment of the present invention;

FIG. 9B shows the front of a switch unit for controlling an ultrasonic output, the switch unit being attached to the handpiece according to the third embodiment;

FIG. 9C is a section view of the switch unit along an IXC-IXC line in FIG. 9B;

FIG. 9D is a rear view of the switch unit;

DETAILED DESCRIPTION OF THE PREFERRED EMBODIMENTS

With reference to accompanying drawings, a variety of types of embodiments of a handpiece for use in ultrasonic treatments and an ultrasonic treatment apparatus with the handpiece, which are according to the present invention, will now be described.

First Embodiment

Referring to FIGS. 1A and 1B to 4, a first embodiment of the handpiece for use in ultrasonic treatments and the ultrasonic treatment apparatus with the handpiece will now be described.

Figures 1A, 1B:
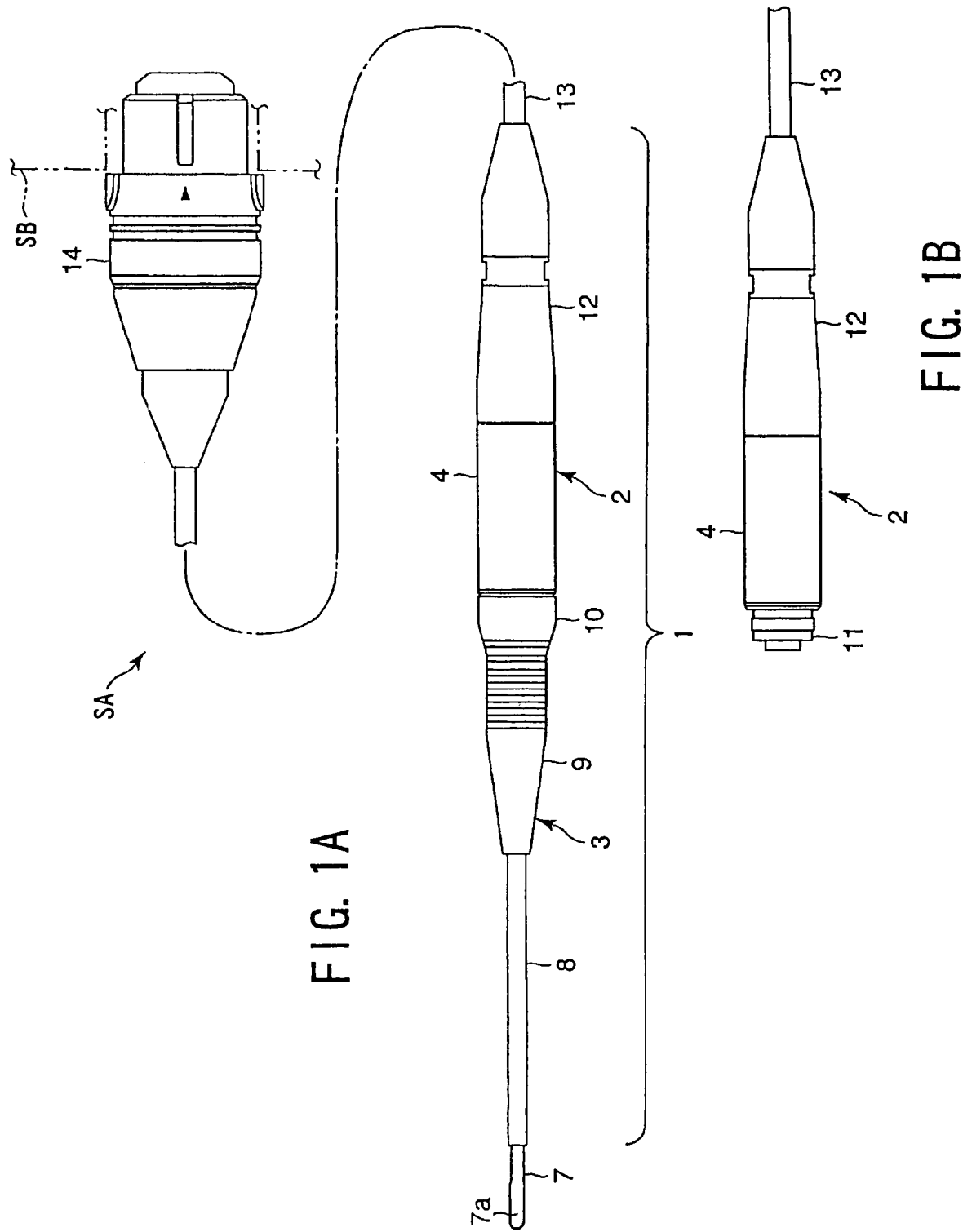
FIG. 1A is a side view showing, partly omitted, an outer appearance of an operation apparatus employed by an ultrasonic treatment apparatus according to a first embodiment of the present invention.
FIG. 1B is a side view showing an outer appearance of a transducer unit composing part of a handpiece employed by the operation apparatus shown in FIG. 1A.

As shown in FIG. 1A, the ultrasonic treatment apparatus in accordance with the present embodiment is provided with an operation apparatus SA and a main unit SB connected to operation apparatus SA in a detachable manner.

The operation apparatus SA is, on the whole, formed into a substantially cylindrical device which is long in its longitudinal direction, compared to the size in its radial direction. Hence, in the present embodiment, a direction along its length of the operation apparatus SA is called "axial direction" and a top side (distal end side) of the operation apparatus SA in the axial direction (the left-sided end side in FIG. 1A) is simply called "top side" and the opposite side to the top side thereof (the right-side end in FIG. 1A) is simply called "base side."

The operation apparatus SA is provided with a handpiece 1, as shown in FIG. 1A. Specifically, the operation apparatus SA is provided with a transducer unit 2, sheath unit 3, cable connector 12, handpiece cable 13 connected to the cable connector 12, and handpiece plug 14 for making detachably the handpiece cable 13 connect to the main unit SB. Of these components, the transducer unit 2 incorporates therein an ultrasonic vibration source (later described) and is formed into have a cylindrical outer appearance. The sheath unit 3 is detachably connected to the distal end of the transducer unit 2 and has a probe (later described). The cable connector 12 is placed at the base end of the transducer unit 2 (on the right end side in FIG. 1A).

Both the transducer unit 2 and the sheath unit 3 compose the handpiece 1. The transducer unit 2 contains various components serving as a casing unit according to the present intention.

FIG. 1B shows a state wherein the sheath unit 3 is removed from the transducer unit 2.

FIGS. 2A to 2F illustrate the internal structure of the transducer unit 2. As illustrated in FIG. 2A, this transducer unit 2 is equipped with a cylindrical cover 4 that has an inner space formed therein, an ultrasonic transducer 5 of bolt-clamped Langevin type incorporated in the cover 4 and formed to generate ultrasonic oscillation, a horn (or horn assembly) 6 (serving as an amplitude amplification element according to the present invention) coupled with a top-side end of the ultrasonic transducer 5 and formed to amplify the amplitude of ultrasonic vibration, and a holder 17 described later. The ultrasonic transducer 5 comprises, for example, six layered piezoelectric elements.

Both the ultrasonic transducer 5 and the horn 6 compose a vibration source according to the present invention, which generates ultrasonic vibration.

The ultrasonic transducer 5 and horn 6 are formed into one integrated unit in advance, and, as described later, the one integrated unit is secured and held in the cover 4 by means of the holder 17 and a later-described fixing portion 15d.

In top-side end of the horn 6, a bottomed screw hole 6a is formed accept a probe. As shown in FIG. 1A, a substantially-rod-formed elongated probe 7 has a base-side end 7b, which is, as shown in FIG. 2A, screwed in the screw hole 6a. An attachment screw end (not shown), which can be coupled with the screw hole 6a of the horn 6, is formed in the base-side end 7b of the probe 7. This attachment screw end can be screwed and fixed in the screw hole 6a of the horn 6 in the transducer unit 2 in a detachable manner, which allows the probe 7 to detachably be coupled with the horn 6 in the transducer unit 2. In consequence, the ultrasonic vibration generated by the ultrasonic transducer 5 is amplified by the horn 6 and then transmitted to the probe 7, whereby the amplified ultrasonic vibration is supplied to a top-side distal treatment device 7a of the probe 7.

The sheath unit 3 is equipped with a sheath 8 serving as a cover member in which part of the probe 7 other than the distal treatment device 7a thereof is placed and a gripping portion 9 coupled with a base-side end of the sheath 8 and formed into a relatively larger shape in radius. In addition, a transducer connector 10 is formed at the base-side end of the gripping portion 9. Hence the gripping portion 9, transducer connector 10, and a top-side potion of the transducer unit 2 provide a portion of the handpiece 1 actually gripped by an operator(s) during surgical operations.

As shown in FIG. 1B, on the top-side end of the transducer unit 2, a unit coupler 11 for detachable coupling with the sheath unit 3 is formed. The unit coupler 11 is formed to be detachable to the transducer connector 10 formed on the base-side end of the sheath unit 3.

Moreover, the cable connector 12 is formed on the base-side end of the cover 4. This cable connector 12 is configured to be connected with one end of the handpiece cable 13 which supplies current from a power supply of the main unit SB to the transducer. The other end of the handpiece cable 13 is coupled with the handpiece plug 14 for connection with the main unit SB. The main unit SB is equipped with a not-shown foot switch for enabling the output from the ultrasonic transducer 5 to be on/off controlled.

Figure 3:
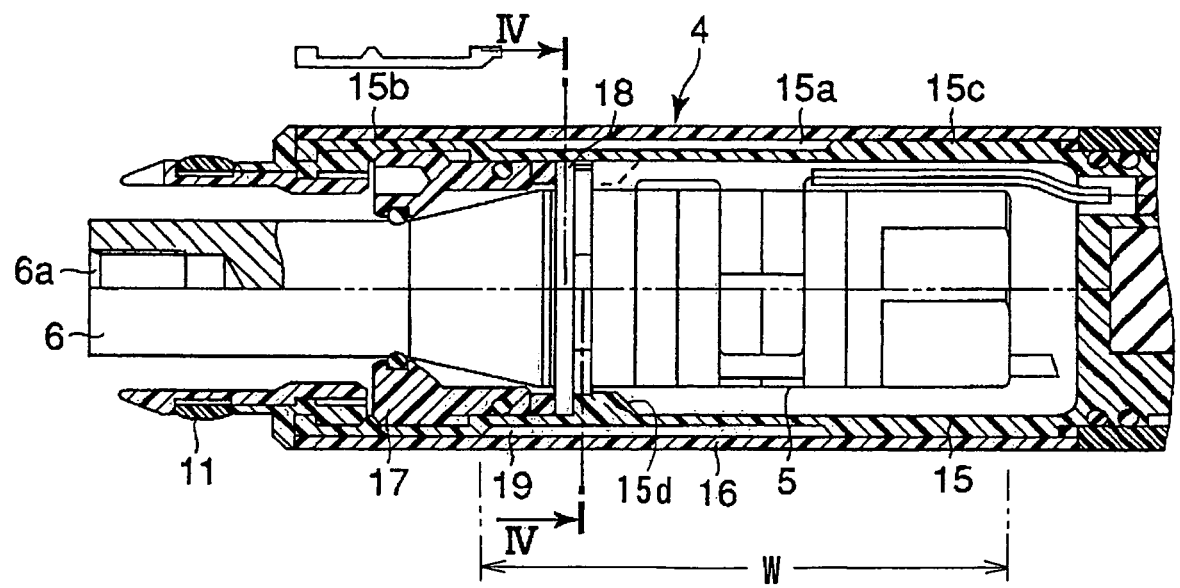
FIG. 3 is an axial section view detaining an essential construction of the transducer unit shown in FIG. 2A.
Figure 4:
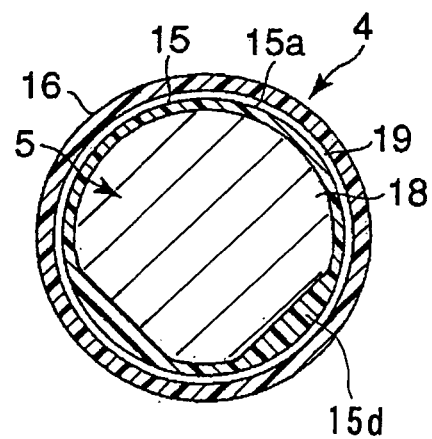
FIG. 4 is a section along an IV-IV line in FIG. 3.

Mainly referring to FIG. 3, an essential part of the transducer unit 2 of the handpiece 1 will now be detailed.

FIG. 3 illustrates a connected portion between the cover 4 and the ultrasonic transducer 5. The cover 4 is structured into a double-layered member, which includes an inner casing 15 and an outer casing 16. On the inner circumferential surface of the top-side end of the inner casing 15, the foregoing holder 17 is secured, which is ring-shaped and serves as a member on which the transducer is attached (held), thus being provided as a transducer coupler. Both the casing 4 and the holder 17 compose the casing unit according to the present invention.

The ultrasonic transducer 5 is equipped with a transducer flange 18 fixed on the top-side end to which the base-side end of the horn 6 is coupled. The transducer flange 18 is made larger in diameter than the remaining axial portion of the transducer 5. This transducer flange 18 is secured on a ring-shaped fixing portion 15d fixedly placed and protruded on and from the inner circumferential surface of the inner casing 15, so that the ultrasonic transducer 5 is fixedly incorporated in the casing 4. In the present embodiment, the axial position of the transducer flange 18 corresponds to a mean position of waves of ultrasonic vibration traveling along the probe 7.

Between the inner and outer casing 15 and 16, there is formed a heat/vibration blocking layer 19 (composing a blocking layer according to the present invention) that reduces or prevents heat and vibration caused by the ultrasonic transducer 5 from being transmitted to the outer surface of the casing 4.

This heat/vibration blocking layer 19 is located in the wall of the casing 4 so as to particularly surround the ultrasonic transducer 19. More concretely, the heat/vibration blocking layer 19 is located so that the layer 19 surely covers a predetermined axial range including, at its center, an axial position facing the transducer flange 18 that is a best heat generation source. In consideration of this fact, an axial top-side end position of this heat/vibration blocking layer 19 (that is, the leftmost position in FIG. 3) is set to a position beyond the base-side end of the horn 6 in an axial direction to the left in FIG. 3 and an axial base-side end position of the layer 19 (that is, the rightmost position in FIG. 3) is set to a position that is over at least the first piezoelectric layer of the ultrasonic transducer 5 in an axial direction to the left in FIG. 3. This positional setting results from that fact that, in the ultrasonic transducer 5, the nearer to the first layer, the more amounts of the heat and vibration to be generated. Hence it is preferable that the heat/vibration blocking layer 19 is as long in the axial direction as possible and its base-side end position is as far as possible from the transducer flange 18. Preferably, for example, as explained a reference W in FIG. 3, the layer 19 is positioned to cover an axial position facing the last piezoelectric layer (e.g., the sixth piezoelectric layer).

The heat/vibration blocking layer 19 will now be detailed in terms of its structure. On an outer circumferential surface of the inner casing 15, a relatively wider ring-shaped recess 15a is formed to run along the surface in the circumferential direction. In addition, of the outer circumferential surface of the inner casing 15, both of a top-side remaining surface portion 15b and a base-side remaining surface portion 15c, which adjoin the recess 15b in the axial direction, are respectively touched to an inner circumferential surface of the outer casing 16 in a fluid-tight manner. This double-layered structure creates, at the position of the recess 19, the foregoing heat/vibration layer 19 the form of which is thin and cylindrical. Hence the heat/vibration layer 19 is formed to run around the ultrasonic transducer 5 and horn 6 (that is, both constitutes an ultrasonic vibration source) in the circumference direction. In this way, it is preferred to form the layer 19 in this full circle structure.

The heat/vibration blocking layer 19 is charged with a medium whose heat conductivity is lower than the materials of the inner and outer casings 15 and 16. In the present embodiment, the medium is air charged air-tightly in the recess 19a between the inner and outer casings 15 and 17, whereby the recess 19a provides a layer of air.

The medium of the heat/vibration layer 19 is not always limited to the air (layer), but any medium can be used, as long as it has a heat and vibration blocking effect. By way of example, heat shield materials such as hard polyurethane rubber and "heat buster TK2 (trademark)" may be employed.

The operations and advantages of the handpiece according to the present invention will now be explained.

When the ultrasonic treatment apparatus is used, its power switch and the foot switch are turned on in sequence, so that the ultrasonic transducer 5 in the handpiece 1 is driven. The vibration due to the ultrasonic wave generated by the ultrasonic transducer 5 is amplified in its magnitude by the horn 6, and then transmitted to the probe 7. That is, the amplified vibration is fed to the distal treatment device 7a of the probe 7. Making the distal treatment device 7a touch anatomy in a region to be treated makes it possible to give the anatomy treatments, such as emulsification, incision, ablation, and coagulation, using the vibration based on ultrasonic waves.

When the ultrasonic transducer 5 is driven to vibrate, the transducer 5 generates heat as well. Especially, when the ultrasonic transducer 5 is driven to continuously oscillate, an amount of energy of this heat and vibration becomes larger considerably. As described, this type of ultrasonic transducer 5 exhibits a tendency that the nearer to the transducer flange 18, the larger amount of heat generated. Hence, in such a situation, an amount of heat to be transmitted from the ultrasonic transducer 5 to the inner casing 15 via the transducer flange 18 and holder 17 becomes large. In addition, heat is also generated from the overall ultrasonic transducer 5 and air-propagated to the inner circumferential surface of the inner casing 15. This transmitted heat also raises the amount of heat accumulated in the inner casing 15. In consequence, driving the ultrasonic transducer 5 in the continuous oscillation mode results in that the inner casing 5 has heat due to the propagating and transmission thereof.

Concurrently, the vibration generated by the ultrasonic transducer 5 which is in continuous oscillation drive transfers to the inner casing 15 via the transducer flange 18 and holder 17. This vibration causes frictional heat between the transducer flange 18 and the holder 17, whereby the frictional heat boosts up the foregoing amount of heat to be transmitted the inner casing 15.

However, in the present embodiment, most of the heat and vibration that have been generated by the continuous drive transmitted to the inner casing 15 is reduced or blocked (insulated) by the heat/vibration blocking layer 19 without fail, resulting in that the heat and vibration to be transmitted to the outer casing 16 is also reduced to a larger degree. In particular, the present embodiment employs the heat/vibration blocking layer 19 positioned to enclose both of the ultrasonic transducer 5 and the horn 6, which thus provides a sure reduction (or blocking) effect for the heat and vibration. Accordingly, an amount of energy of the heat and vibration, which have been generated by the ultrasonic transducer 5 and transmitted to the outer casing 16, that is, the outer surface of the transducer unit 2, is lowered without fail. Hence, when gripping the handpiece 1, operators, such as surgeons, scarcely have any influence on the operator's operations for the ultrasonic treatments. That is, since the temperature on the handpiece 1 is reduced down, the handpiece 1 is easy to handle. Since the vibration on the handpiece 1 is lessened or almost prevented, a skin friction coefficient on the handpiece 1 is not reduced, thus avoiding the handpiece 1 from being slippery, thus providing no adverse effect on operations for the treatments toward anatomy.

As a result, the ultrasonic treatment apparatus according to the present embodiment has the following advantages.

The heat/vibration blocking layer 19 is disposed between the inner and outer casings 15 and 16 (that is, in the wall portion) of the casing 4 of the handpiece 1 so that the layer 15 enclose the ultrasonic transducer 5. This heat/vibration blocking layer 19 is therefore able to block or reduce the transmission of the heat and vibration from the fixing portion 15d for holding the transducer flange 18 of the ultrasonic transducer 5, even when the ultrasonic transducer 5 is driven in a continuous oscillation mode. The heat and vibration from the fixing portion 15d for holding the transducer flange 18 of the transducer 5 are blocked (prevented or reduced) from being transmitted to the outer surface of the casing 4.

In addition, the location of the heat/vibration blocking layer 19 in the fall of the casing 4 is decided with taking it into account the position of the transducer flange 18 that is best easy to heat. Positioning the layer 19 in this way provides a high heat/vibration blocking effect. Thus the sizes (particularly, an axial length and a radial length (thickness)) of the heat/vibration blocking layer 19 formed in within the handpiece 1 can be lessened down to necessary quantities, that is, minimized. The overall handpiece 1 can be avoided from being made larger, that is, made more compact. Particularly, compared to the conventional configuration described with the publication 1, the heat/vibration blocking structure can be provided. It is thus possible to simplify the structure of the overall handpiece 1, thereby being made compact and less weighing.

Further, the heat/vibration layer 19 according to the present embodiment is an air layer air-tightly enclosed by the inner and outer casings 15 and 16 and functions as a heat-insulation and vibration-insulation structure whose heat conductivity is lower than the materials that compose the inner and outer casings 15 and 16. Hence the heat/vibration blocking layer 19 is effective for not only blocking the heat and vibration caused in response to continuously driving the ultrasonic transducer 5 but also blocking steam accompanying with autoclave sterilization. Specifically, when the handpiece 1 is subjected to the autoclave sterilization, the steam may penetrate resin parts of the outer casing 16. However, the heat/vibration blocking layer 19 operates to block off or interrupt of the transmission of the steam. It is therefore effective for improving resistance against the autoclave sterilization.

Second Embodiment

Referring to FIGS. 5A, 5B, and 5C to FIG. 8, a second embodiment of the present invention will now be described.

The second embodiment relates to another example of the sheath unit 3 of the handpiece 1 of the ultrasonic treatment apparatus according to the foregoing first embodiment (refer to FIGS. 1A and 1B to FIG. 4).

Incidentally the transducer unit 2 in the second embodiment has the same configuration as that in the first embodiment, so the identical or similar components to those in the first embodiment will be referred by the same reference numerals, whereby those components are omitted from being described.

The sheath unit 3 according to the second embodiment is provided with, as shown in FIGS. 5A to 5C, a sheath 21 with a manually operated switch. The sheath 21 has a radio-frequency output transmission member 22 transmitting a radio-frequency output to the probe 7 and a switch 23 controlling the radio-frequency output so that it is switched on or off.

The sheath 21 includes a switch loaded portion 24 placed on part of an outer circumferential surface of the gripping portion 9. On the top-side end of this switch loaded portion 24, a switch 23 is placed. The base-side end of the switch loaded portion 24 is formed as a cable connector 25.

Figures 6A, 6B:
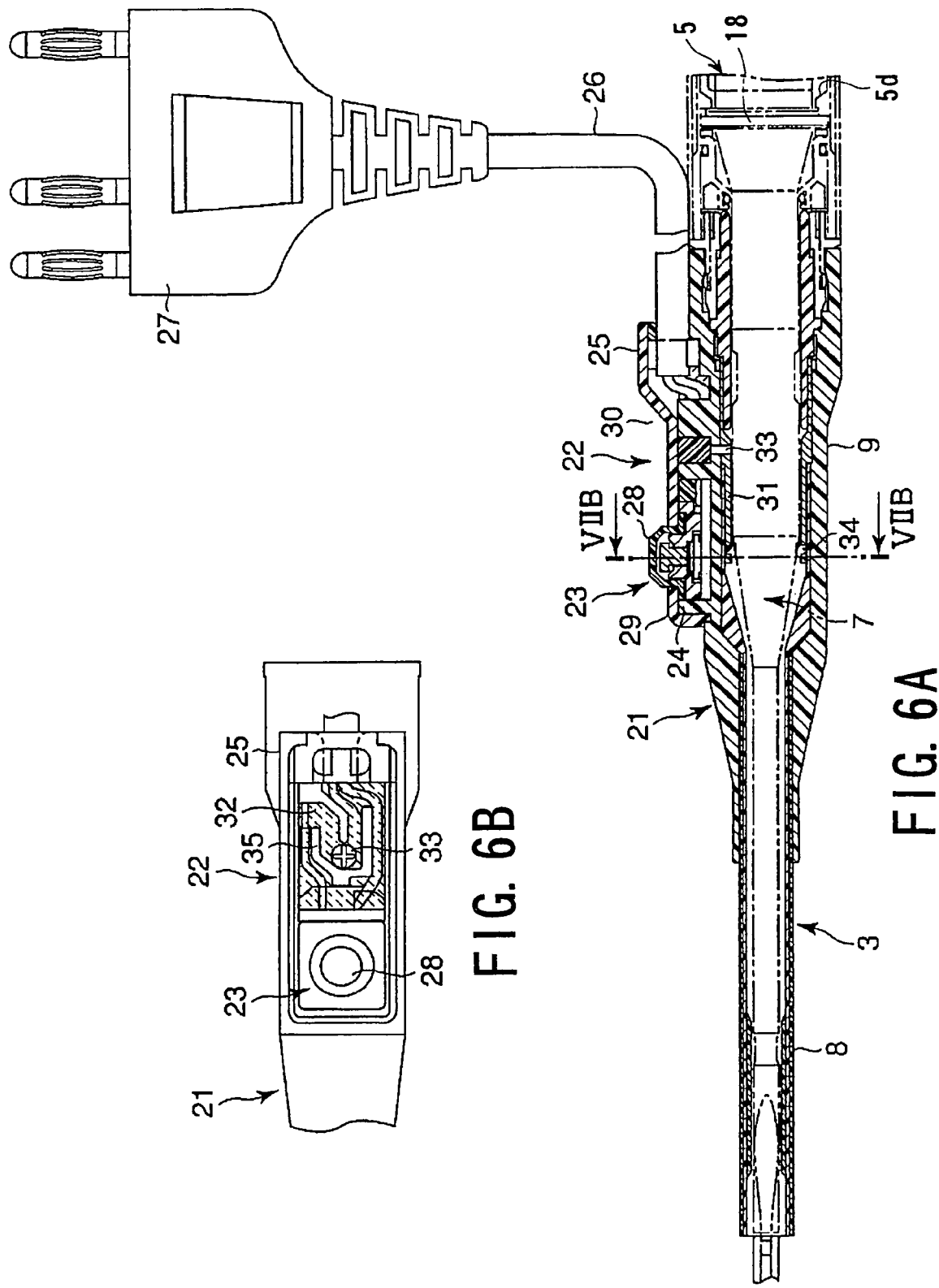
FIG. 6A is an axial section view showing the internal structure of a sheath unit composing part of the handpiece in the second embodiment.
FIG. 6B is a plane view illustrating a switch attachment of the sheath unit shown in FIG. 6A.

As shown in FIG. 6A, the cable connector 25 is connected to one end of a connection cable 26 leading to a radio-frequency cautery apparatus. The other end of the connection cable 26 is connected with a connection plug 27 connected with the radio-frequency cautery apparatus.

The switch 23 is provided with a push button 28 and a base member 29 supporting the push button 28 such that the button 28 can be shifted up and down. This push button 28 is always pushed upward (outward) by not-shown pushing means, such as blade spring, to protrude from the base member 29. When the push button 28 is shifted upward to take a protruding attitude, the switch 23 provides its switch contact 23a as a normally open contact whose contact is kept to an open position, as shown in FIG. 8. In contrast, when pushing the push button 28, its switch contact becomes closed.

Furthermore, in the hand piece 1 according to the present embodiment, as shown in FIGS. 7A and 5B, a stepped-down portion 30 is formed on the upper surface of the switch loaded portion 24 so that the height is stepped down to come closer to the gripping portion 9. The push button 28 is designed to have a specific height lower than the height of the outer surface of the gripping portion 9. This enables a user who grips the gripping portion 9 with user's fingers fitted well to the gripping portion 9, whereby feelings on the user's fingers allows the push button 28 to be found on the switch 23 without user's watching of the push button 28.

The radio-frequency output transmission member 22 of the sheath 21 is provided with a cylindrical electrode member 31 disposed around the probe 7, a wiring connector 33 secured to a base-side end of the electrode member 31 and connected to a connection wire 32 of the switch 23, and a ring-shaped conductive rubber 34 fixed to a top-side end of the electrode member 31 and connected to the probe 7. The connection wire 32 includes a printed wiring electrode 35 formed on, for example, a glass epoxy resin substrate. The printed wiring electrode 35 has, as shown in FIG. 6B, bent portions to adjust the lengths of the wires.

The wiring connector 33 is made up of for example a metal-made fixating screw. This fixing screw is able to establish an electrical connection between the wiring connector 33 and the electrode member 31. The probe 7 is inserted through the sheath unit 3 for assembly. When the probe 7 is assembled at specified assembling positions, the conductive rubber 34 on the top-side end of the electrode member 31 is pressed onto an outer circumferential surface of the probe 7, whereby an electrical connection is realized between the conductive rubber 34 and the probe 7.

In the handpiece 1 of the present embodiment, design is made such that the radio-frequency output is on/off-controlled in response to a pushing operation toward the push button 28 of the switch 23. This push button 28 can be operated independently of the oscillated states of the ultrasonic transducer 5. In cases where the push button 28 is in its non-pushed state, the radio-frequency output is kept off, while in cases where the push button 28 is pushed down, the radio-frequency output is turned on.

The operations and advantage gained from the above configurations will now be explained.

Like the first embodiment, when the ultrasonic treatment apparatus is used, its power switch and the foot switch are turned on in sequence, so that the ultrasonic transducer 5 in the handpiece 1 is driven. In the similar manner to that in the first embodiment, the vibration due to the ultrasonic wave generated by the ultrasonic transducer 5 is amplified in its magnitude by the horn 6, and then transmitted to the probe 7. That is, the amplified vibration is fed to the distal treatment device 7a of the probe 7. Making the distal treatment device 7a touch anatomy in a region to be treated makes it possible to give the anatomy treatments, such as incision, ablation, and coagulation, using the vibration based on ultrasonic waves.

Moreover, like the first embodiment, during the continuous oscillation of the ultrasonic transducer 5, the heat and vibration coming from the fixing portion 15d for holding the transducer flange 18 of the ultrasonic transducer 5 are blocked or insulated (prevented or lessened) by the heat/vibration blocking layer 19 positioned around the ultrasonic transducer 5. Hence the heat and vibration transmitted from the transducer 5 to the outer surface of the casing 4 are reduced to a great extent.

In the handpiece 1 according to the present embodiment, push operations for the push button 28 of the switch 23 permit the radio-frequency (RF) output to be on/off-controlled irrelevantly of the oscillated states of the ultrasonic transducer 5. That is, when no push operation is given to the push button 28 so that the push button 28 is held in its non-pushed state, the radio-frequency output is in an off-state, while the push button 28 is pushed down, the radio-frequency output is turned on.

As a result, there are provided various advantages in this embodiment. Since the handpiece 1 uses the transducer unit 2 that is identical to that in the first embodiment, the heat/vibration blocking layer 19 is effective for blocking (preventing or reducing) the transmission of the heat and vibration from the ultrasonic transducer 5 to the casing 4, even when the transducer 5 is driven in a continuous oscillation mode.

Moreover, in the handpiece 1 according to the present embodiment, the sheath unit 3 is provided with the sheath 21 with the manually operated switch, and the sheath 21 is provided with the radio-frequency output transmission member 22 and the switch 3 for controlling the on/off states of the radio-frequency output. Hence pushing and non-pushing the push button 28 make it possible to control on/off states of the radio-frequency output. In cases where the radio-frequency output is in its on-state, the radio-frequency output is transmitted to the probe 7 via the wiring connector 33 of the switch 23, electrode member 31 around the probe 7, and ring-shaped conductive rubber 34 at the tip end of the electrode member 31, so that treatments can be done based on the radio-frequency output.

Hence it is possible to concurrently use both the ultrasonic treatments that use the ultrasonic vibration transmitted from the transducer 5 in the transducer unit 2 to the probe 7 and the radio-frequency treatments that use the radio-frequency output transmitted from the sheath unit 3 to the probe 7 in response to the on/off control commanded by manually operating the switch 23. As a result, using only the same one compact handpiece 1, the user is able to perform both the ultrasonic treatments and the radio-frequency treatments. This eliminates the need for using separate two handpiece sets for ultrasonic treatments and radio-frequency treatments, thus improving efficiency in operations.

In addition, the connection wires 32 of the switch 32 can be adjusted in terms of their wire lengths by the bent portions on the printed wiring electrode 35. Thus the radio-frequency output can be avoided from being short-circuited.

Third Embodiment

Figure 12:
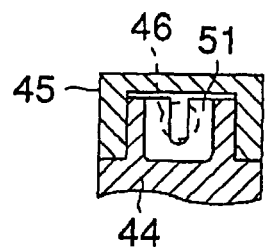

Referring to FIGS. 9A to 9D and to FIG. 12, a third embodiment of the present invention will now be described.

This third embodiment provides an ultrasonic treatment apparatus provided with the handpiece 1 the outer surface of which detachably accepts an external switch unit 41 for controlling an ultrasonic output.

Incidentally the handpiece 1 in the third embodiment has the same configuration as that in the first embodiment, so the identical or similar components to those in the first embodiment will be referred by the same reference numerals, whereby those components are omitted from being described.

As shown in FIG. 9A, the handpiece 1 according to the present embodiment is provided with the switch unit 41 detachably disposed on the base-side end of the gripping portion 9 composing part of the sheath unit 3. This switch unit 41 includes a switch 42 for controlling the ultrasonic output.

The switch 42 has a push button 43 and a substantially flat base member (switch sustainer) 44 sustaining the push button 43 in such a manner that the button 43 can be shifted up and down. A base-side end of the base member 44 is formed as a cable connecting portion 45, which is connected to one end of a connection cable 46 for controlling an ultrasonic output. The other end of the connection cable 46 is coupled with a connection plug (not shown) which can be linked with a main frame (not shown) of the ultrasonic treatment apparatus.

The base member 44 has an upper surface including a stepped-down portion 47 located on the top side of the upper surface and formed to have a height lower than the cable connecting portion 45. On the stepped-down portion 47 is provided a switch loaded portion 48 with which a switch 42 is loaded. The push button 43 is designed to have a specific height lower than the height of the outer surface of the cable connecting portion 45. This enables a user who grips the gripping portion 9, together with the switch unit 41, with user's fingers fitted well to the gripping portion 9, whereby the feelings on the user's fingers allows the push button 43 to be found on the switch 42 without user's watching of the push button 43.

The push button 43 is always pushed upward (outward) by not-shown pushing means, such as blade spring, to protrude from the base member 44. When the push button 43 is shifted upward to take a protruding attitude, the switch 42 provides its switch contact as a normally open contact whose contact is kept to an open position, like the switch 23 according to the second embodiment (refer to the switch contact 23a in FIG. 8). In contrast, when pushing the push button 28, its switch contact becomes closed.

Accordingly, the radio-frequency output is on/off-controlled in response to pushing operations toward the push button 43 of the switch 42 of the switch unit 41. In cases where the push button 43 is in its non-pushed state, the radio-frequency output is kept off, while in cases where the push button 43 is pushed down, the radio-frequency output is turned on.

Furthermore, as shown in FIGS. 9B and 9C, the switch unit 41 includes mounting arms 49 each of which is formed to perpendicularly protrude from the base member 44 on both axial sides of the top-side end thereof. The mounting arms 49 are in charge of mounting the switch unit 41 around the handpiece 1 in a rotatable manner about the axis thereof. These mounting arms 49 are mounted to gasp the base-side end of the gripping portion 9 of the sheath unit 3.

As shown in FIGS. 9C and 9D, a rubber plate (rotation stopper) 50 is fixedly placed on a lower surface of the base member 44 which is made to touch the handpiece 1. This rubber plate 50 serves as a frictional member to stop the rotation of the base plate 44 by enhancing the friction between the base plate 44 and the handpiece 1. Thus the friction between the rubber plate 50 and the handpiece 1 can be used to position the base plate 44, that is, the switch unit 41, at any angular position in the circumferential direction about the axis of the handpiece 1.

Figure 10:
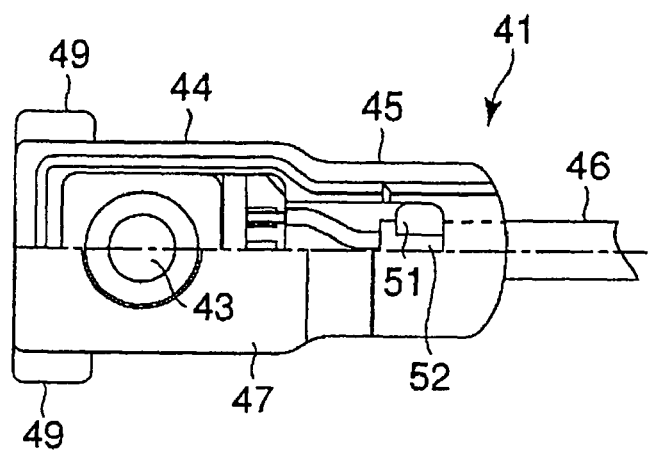
FIG. 10 is a half-sectional view of the switch unit.
Figure 11:
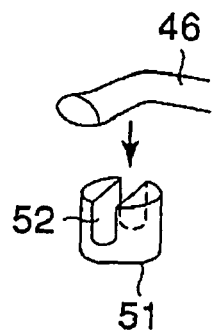
FIGS. 11 and 12 are, respectively, a perspective view and a longitudinal section view showing a condition in which a cable is attached to a cable pulling-stop member in the switch unit.

Furthermore, as shown in FIG. 10, the cable connecting portion 45 is provided with a substantially U-shaped cable coming-off stopper 51, which prevents the connection cable 46 from coming off. This cable coming-off stopper 51 has a U-shaped groove 52 formed therethrough, whose width is narrower than the diameter of the connection cable 46, as shown in FIG. 11. The connection cable 46, which is connected to the switch 42, is forcibly inserted in the U-shaped groove 52 of the stopper 51, whereby the connection cable 46 is prevented from coming off from the switch 42.

The operations and advantage gained from the above configurations will now be explained.

When the ultrasonic treatment apparatus is used, its power switch and the push button 43 of the switch 42 are operated into their "on" states in sequence, so that the ultrasonic transducer 5 in the handpiece 1 is driven. In the similar manner to that in the first embodiment, the vibration due to the ultrasonic wave generated by the ultrasonic transducer 5 is amplified in its magnitude by the horn 6, and then transmitted to the probe 7. That is, the amplified vibration is fed to the distal treatment device 7a of the probe 7. Making the distal treatment device 7a touch anatomy in a region to be treated makes it possible to give the anatomy treatments, such as incision, ablation, and coagulation, using the vibration based on ultrasonic waves.

Moreover, like the first embodiment, during the continuous oscillation of the ultrasonic transducer 5, the heat and vibration coming from the fixing portion 15d for holding the transducer flange 18 of the transducer flange 18 of the ultrasonic transducer 5 are insulated or blocked (prevented or lessened) by the heat/vibration blocking layer 19 positioned around the ultrasonic transducer 5. Hence the heat and vibration transmitted from the transducer 5 to the outer surface of the casing 4 are reduced to a great extent.

As a result, there are provided various advantages in this embodiment. Since the handpiece 1 uses the transducer unit 2 that is identical to that in the first embodiment, the heat/vibration blocking layer 19 is effective for blocking (preventing or reducing) the transmission of the heat and vibration from the ultrasonic transducer 5 to the casing 4, even when the transducer 5 is driven in a continuous oscillation mode.

A further advantage comes from the switch unit 41. Because the handpiece 41 of the present embodiment has the switch unit 41 for controlling the ultrasonic output, which is a detachable external switch unit, the switch unit 41 can be installed or removed at any directional position through one-touch operation.

Another advantage results from fixedly disposing the rubber plate 50 on the lower surface of the base member 44. This disposal gives an appropriate rotational force to the switch unit 41.

Further, the connection cable 46 is prevented from coming off from the switch unit 41 with the aid of both of the cable coming-off stopper 51 on the cable connecting portion 45 and the U-shaped groove 52 formed on the stopper 51. This structure not only improves the strength of the cable connecting portion 45 of the switch unit 41 but also facilitates assembly.

Fourth Embodiment

Figure 13A:
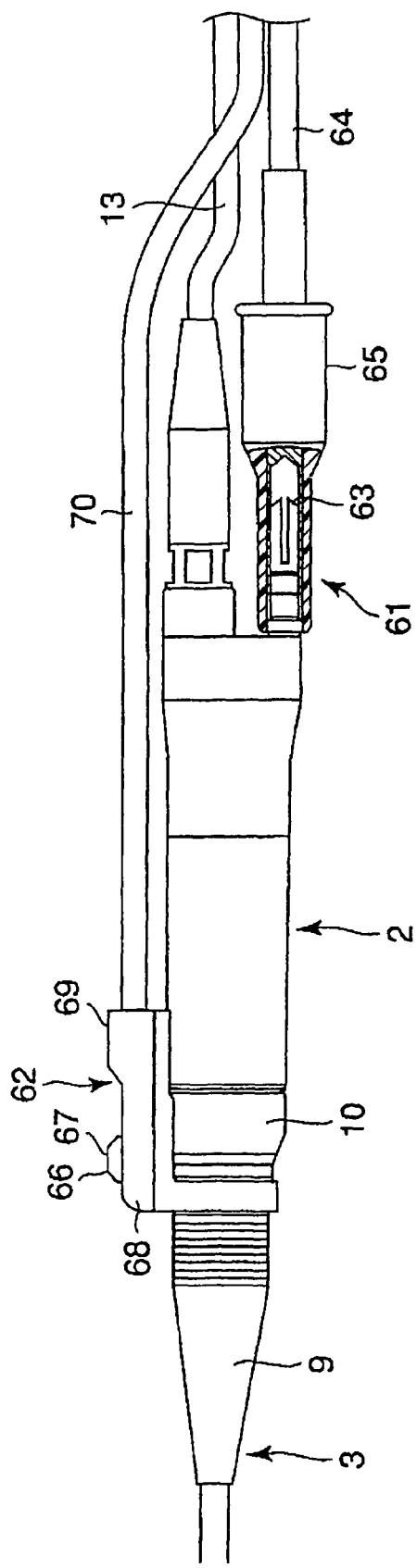
FIG. 13A is a side view showing an outer appearance of a main part (focusing on a handpiece) of an operation apparatus adopted by an ultrasonic treatment apparatus according to a fourth embodiment of the present invention.
Figure 13B:
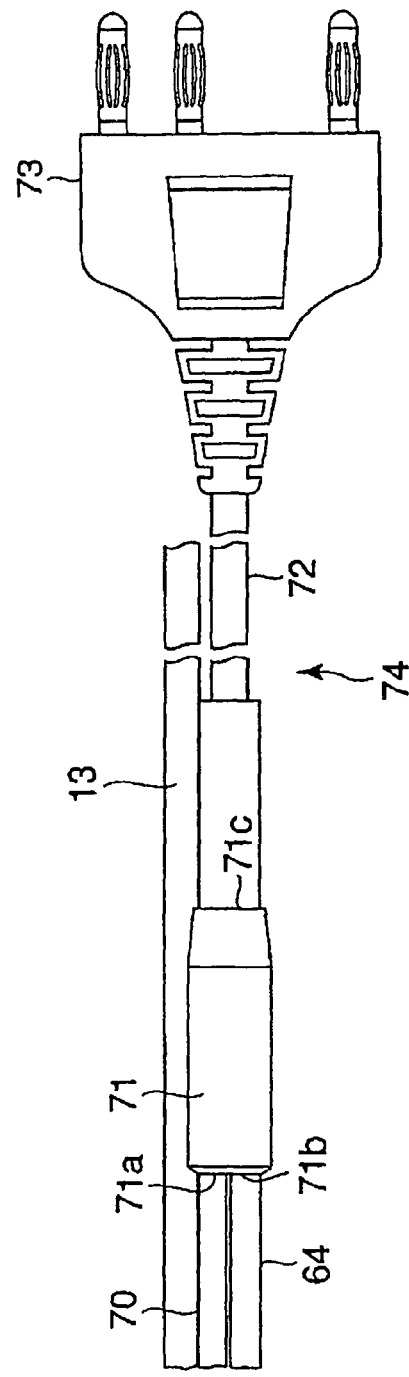
FIG. 13B is a plan view showing an essential configuration of a cable unit adopted by the handpiece in the fourth embodiment.
Figure 14:
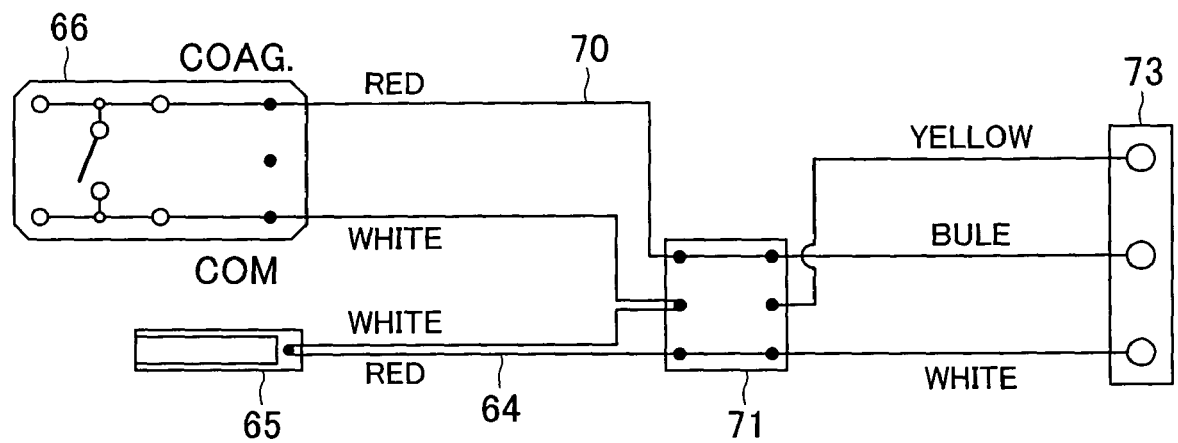
FIG. 14 outlines an electrical diagram given to the handpiece adopted by the ultrasonic treatment apparatus according to the fourth embodiment.

Referring to FIGS. 13A, 13B and 14, a fourth embodiment of the present invention will now be described.

The present embodiment provides an ultrasonic treatment apparatus with a handpiece modified from the handpiece 1 according to the first embodiment. In the third embodiment, the similar or identical components to those of the handpiece 1 in the first embodiment will be referred by the same reference numerals, with their explanations omitted.

As shown in FIG. 13A, a handpiece 1 according to the present embodiment is provided with the transducer unit 2 whose base-side end is integrated with a radio-frequency output transmission member 61 and the sheath unit 3 on which an external switch unit 62 for controlling the radio-frequency output is disposed in a detachable manner.

Of these, the radio-frequency output transmission member 61 includes a radio-frequency output terminal 63 protruding backward from a side surface of the base-side end of the transducer unit 2. To this terminal 63 is connected a connector 65 linked with one end of a connection cable 64 for outputting a radio-frequency output.

On the other hand, the external switch unit 62 comprises a switch 66 for controlling the radio-frequency output. This switch 66 is equipped with a push button 67 and a substantially plate-like base member (switch sustainer) 68 sustaining the push button 67 such that the button 67 can be moved up or down. A base-side end of the base member 68 is formed as a cable connecting portion 69. To this cable connecting portion 69 is connected one end of a connection cable 70 for outputting the radio-frequency output.

As shown in FIGS. 13A and 13B, the handpiece 1 is equipped with additional components including a relay connector 71, a connection cable 72, and a connection plug 73, which are united into one unit as a cable unit 74.

The relay connector 71 comprises two output terminals 71a and 71b and one input terminal 71c. Of these terminals, the output terminals 71a and 71b are coupled with the other end of the connection cable 70 for controlling the radio-frequency output and the other end of the connection cable 64 for the radio-frequency output, respectively. The input terminal 71c is solely connected with one end of the connection cable 72. The remaining other end of the connection cable 72 is coupled with the connection plug 73, which is linked with the main frame of a not-shown radio-frequency cautery apparatus. Hence both of the connection cables 64 and 70 can be branched at the relay connector 71, while their base portions are combined into the one cable unit 74. FIG. 14 shows an electrical circuit of this handpiece 1.

The operations and advantage gained from the above configurations will now be explained.

When the ultrasonic treatment apparatus is used, its power switch and the foot switch are turned on in sequence, so that the ultrasonic transducer 5 in the handpiece 1 is driven. In the similar manner to that in the first embodiment, the vibration due to the ultrasonic wave generated by the ultrasonic transducer 5 is amplified in its magnitude by the horn 6, and then transmitted to the probe 7. That is, the amplified vibration is fed to the distal treatment device 7a of the probe 7. Making the distal treatment device 7a touch anatomy in a region to be treated makes it possible to give the anatomy treatments, such as incision, ablation, and coagulation, using the vibration based on ultrasonic waves.

Further, like the first embodiment, during the continuous oscillation of the ultrasonic transducer 5, the heat and vibration coming from the fixing portion 15d for holding the transducer flange 18 of the transducer flange 18 of the ultrasonic transducer 5 are insulated or blocked by the heat/vibration blocking layer 19 positioned around the ultrasonic transducer 5. Hence the heat and vibration transmitted from the transducer 5 to the outer surface of the casing 4 are reduced to a great extent.

Still further, in this handpiece 1, responsively to pressing operations toward the push button 67 belonging to the switch 66 of the external switch unit 62, the radio-frequency output is controlled in an on/off manner independently of the drive of the ultrasonic transducer 5. That is, the push button 67 can be operated solely for controlling the radio-frequency output. When the push button 67 is held with no pressing operation given, the radio-frequency output is "off," while the radio-frequency output is turned "on" in reply to a pressing operation toward the push button 67.

As a result, there are provided various advantages in this embodiment. Since the handpiece 1 uses the transducer unit 2 that is identical to that in the first embodiment, the heat/vibration blocking layer 19 is effective for blocking the transmission of the heat and vibration from the ultrasonic transducer 5 to the casing 4, even when the transducer 5 is driven in a continuous oscillation mode.

In addition, in the present handpiece 1, the radio-frequency output transmission member 61 is formed at the base-side end of the transducer unit 2 and the external switch unit 62 for control of the radio-frequency output is detachably attached to the sheath unit 3. Hence this handpiece 1 can be used in common for both of ultrasonic treatments, which are conducted with the use of the ultrasonic vibration transmitted to the probe 7 from the ultrasonic transducer 5 in the transducer unit 2, and radio-frequency treatments, which are conducted with the use of radio-frequency output transmitted to the probe 7 by causing the switch 66 of the external switch unit 62 to control the radio-frequency output in an on/off manner. As a result, using only the same one compact handpiece 1, the user is able to perform both the ultrasonic treatments and the radio-frequency treatments. This eliminates the need for using separate handpiece sets for ultrasonic treatments and radio-frequency treatments, thus improving efficiency in operations.

Moreover, the ultrasonic treatment apparatus is provided with the cable unit 74 into which the switch unit 62, connection cables 70 and 64, relay connector 71, connection cable 72, and connection plug 73 are formed into one unit. Hence the connections and wiring of the cables can be simplified.

The present invention may be embodied in other specific forms without departing from the spirit or essential characteristics thereof. The present embodiments are therefore to be considered in all respects as illustrative and not restrictive, the scope of the present invention being indicated by the appended claims rather than by the foregoing description and all changes which come within the meaning and range of equivalency of the claims are therefore intended to be embraced therein.

Industrial Availability

The present invention can be utilized in the field of manufacturing and using the ultrasonic treatment apparatus equipped with a handpiece which is used for giving treatments to anatomy to be treated under the ultrasonic vibration.

What is claimed is:

1. An ultrasonic treatment apparatus for medical procedures on an object being treated, comprising:
   a transducer unit that includes an ultrasonic transducer generating ultrasonic vibration and having an axial end outputting the ultrasonic vibration therefrom, a flange attached to the ultrasonic transducer so as to extend from the axial end of the ultrasonic transducer in a radial direction of the ultrasonic transducer, and an amplitude amplification element coupled with the axial end of the ultrasonic transducer to receive the ultrasonic vibration generated by the ultrasonic transducer and to amplify an amplitude of the ultrasonic vibration, the amplitude amplification element having an axial tip end from which the amplified ultrasonic vibration is outputted;
   a probe having both an axial base-side end connectable with the axial tip end of the amplitude amplification element and an axial tip end at which a treatment portion is provided so that the amplified ultrasonic vibration is transmitted to the treatment portion;
   an inner casing that has an inner wall surface to provide an inner space and an outer circumferential surface, the inner casing covers at least part of the amplitude amplification element and the flange, the ultrasonic transducer being accommodated in the inner space along an axial direction of the inner casing, the flange being fixed to the inner wall surface; and
   an outer casing that has an inner circumferential surface to provide an inner space in which the inner casing is accommodated,
   wherein the outer circumferential surface of the inner casing and the inner circumferential surface of the outer casing air-tightly come in contact with each other, and
   the inner and outer casings have a recess formed therebetween, the recess having a ring-shaped section extending perpendicularly to the axial direction and extending in the axial direction such that the recess provides a blocking layer being charged air-tightly with air and blocking transmission of heat and vibration from the inner casing to the outer casing, the blocking layer having a length that covers both the flange and at least part of the ultrasonic transducer in the axial direction.

2. The ultrasonic treatment apparatus according to claim 1, wherein the recess is formed on the outer surface of the inner casing.

3. The ultrasonic treatment apparatus according to claim 2, wherein the blocking layer is lower in heat conductivity than the inner and outer casings.

4. The ultrasonic treatment apparatus according to claim 2, wherein the probe is a substantially rod-shaped probe whose both ends serve as the base-side end and the treatment portion, wherein the base-side end is coupled with the amplitude amplification element in the axial direction.

5. The ultrasonic handpiece according to claim 4, comprising a sheath unit provided with
a sheath enclosing the probe in the axial direction,
a detachable member disposed on a base-side end of the sheath and detachably coupled with a top-side end of the casing unit;
a radio-frequency output transmission member transmitting the radio-frequency output to the probe; and
a switch controlling on/off states of the radio-frequency output.

6. The ultrasonic handpiece according to claim 5, wherein the sheath unit is equipped with
a cylindrical electrode member disposed around the prove in an axial direction of the handpiece,
a wiring connector fixed on a base-side end of the electrode member and connected with a connection wiring of the switch, and
a ring-shaped conductive rubber fixed at a top-side end of the electrode member and connected with the prove.

7. The ultrasonic handpiece according to claim 6, wherein the connection wiring of the switch includes a wiring electrode on a printed substrate, the wiring electrode having a bent-shaped portion to adjust a length of the wiring.

8. The ultrasonic handpiece according to claim 7, wherein the switch has a push button on a loaded portion of the switch of which height is lower than an outer surface of a gripping portion of the handpiece so that the push button has a height lower than the outer surface of the gripping portion.

9. The ultrasonic handpiece according to claim 7, wherein the sheath unit comprises a substantially U-shaped cable coming-off member preventing the connection cable from coming off, wherein the cable coming-off member has a groove into which a cable connected to the switch is forcibly inserted.

10. An ultrasonic handpiece according to claim 4, comprising
a sheath unit provided with
a sheath enclosing the probe in an axial direction of the handpiece, and
a detachable member disposed on a base-side end of the sheath and detachably coupled with a top-side end of the oscillation source; and
a switch unit detachably secured on the sheath unit provided with
a switch sustainer sustaining the switch,
a mounting arm mounting the switch sustainer on the handpiece to permit the switch sustainer to rotate in a direction about an axis of the sheath, and
a rotation stopper secured on a surface of the switch sustainer coming in contact with the sheath unit and formed to stop the switch sustainer at any angular position in the direction about the axis of the sheath.

11. The ultrasonic handpiece according to claim 10, wherein the rotation stopper is composed of a plate-shaped frictional member having friction against the handpiece to stop the rotation of the switch sustainer.

12. An ultrasonic handpiece according to claim 4, comprising
a sheath unit provided with
a sheath enclosing the probe in an axial direction of the handpiece, and
a detachable member disposed on a base-side end of the sheath and detachably coupled with a top-side end of the casing unit,
wherein the casing unit comprises a radio-frequency output transmission member transmitting a radio-frequency output to the probe and the sheath unit comprises a switch controlling an on/off state of the radio-frequency output.

13. The ultrasonic handpiece according to claim 12, comprising:
a radio-frequency output terminal connected to the radio-frequency output transmission member;
a first cable for controlling the radio-frequency output, one end of the first cable being connected with the switch;
a second cable for transmitting the radio-frequency output, one end of the second cable being detachably connected to the radio-frequency output terminal;
a relay connector having not only two output terminals to which both of a remaining end of the first cable and a remaining end of the second cable are connected, respectively, but also a single input terminal; and
a single connection cable of which one end is connected to the input terminal and of which other end is connected to a connection plug.

14. The ultrasonic handpiece according to claim 13, wherein the switch, first and second cables, relay connector, connection cable, and connection plug are united into one unit.

15. The ultrasonic treatment apparatus according to claim 2, wherein:
the ultrasonic transducer is formed by a plurality of piezoelectric layers each generating the ultrasonic vibration and is layered one on another to form a substantially rod shape having the axial end in a layered direction of the piezoelectric layers serving as the axial direction,
each of the inner and outer casings is formed into an approximately cylindrical shape,
the blocking layer is formed to be cylindrical between the inner and outer casings, to have a predetermined length in the axial direction, and extend to cover both the flange and at least a first piezoelectric layer of the ultrasonic transducer in the axial direction, and
the transducer unit comprises a holder holding the ultrasonic transducer and the amplitude amplification element within the inner casing using the flange.

16. The ultrasonic treatment apparatus according to claim 15, wherein the probe is a substantially rod-shaped probe whose both ends serve as the base-side end and the treatment portion, wherein the base-side end is coupled with the amplitude amplification element in the axial direction.

17. The ultrasonic treatment apparatus according to claim 15, wherein the blocking layer has an end extending toward the ultrasonic transducer in the axial direction, the end of the blocking layer being positioned to reach the last piezoelectric layer of the ultrasonic transducer in the axial direction.

18. The ultrasonic treatment apparatus according to claim 15, wherein the blocking layer has an end extending toward the amplitude amplification element in the axial direction, the end of the blocking layer being beyond the flange in the axial direction.

19. The ultrasonic treatment apparatus according to claim 15, wherein the blocking layer has a first end extending toward the ultrasonic transducer in the axial direction, the first end of the blocking layer being positioned to reach the last piezoelectric layer of the ultrasonic transducer in the axial direction, and a second end extending toward the amplitude amplification element in the axial direction, the second end of the blocking layer being positioned to reach a predetermined position beyond the flange in the axial direction.

20. An ultrasonic treatment apparatus for medical procedures on an object being treated, comprising:
 a vibration source equipped with
  an ultrasonic transducer formed by a plurality of piezoelectric layers each generating ultrasonic vibration and being layered one on another to form a substantially rod shape having both ends in a layered direction serving as an axial direction, a flange attached to the ultrasonic transducer to extend in a radial direction of the ultrasonic transducer, from one of the ends of the ultrasonic transducer, and
  an amplitude amplification element coupled with the one of ends of the ultrasonic transducer and formed to amplify an amplitude of the ultrasonic vibration generated by the transducer;
 a casing unit equipped with
  a casing formed into an approximately cylindrical shape, and
  a holder holding the vibration source within the casing using the flange; and
 a substantially rod-shaped probe whose both axial ends serve as a base-side end and a top-side distal treatment portion, wherein the base-side end is coupled with the amplitude amplification element to transmit the ultrasonic vibration to the top-side distal treatment portion,
 wherein the casing has an inner casing that has an inner wall surface to provide an inner space and an outer circumferential surface, at least part of the amplitude amplification element, the flange, and the ultrasonic transducer being accommodated in the inner space in the axial direction, the flange being fixed to the inner wall surface; and
 an outer casing that has an inner circumferential surface to provide an inner space in which the inner casing is accommodated;
 the outer circumferential surface of the inner casing and the inner circumferential surface of the outer casing air-tightly come in contact with each other;
 the inner and outer casings have a recess formed therebetween, the recess having a ring-shaped section extending perpendicularly to the axial direction and extending in the axial direction such that the recess provides an blocking layer blocking transmission of heat and vibration from the inner casing to the outer casing, the blocking layer being charged air-tightly with air and having a length that covers both the flange and at least part of the ultrasonic transducer in the axial direction; and
 the blocking layer has first and second ends, the first end extending toward the ultrasonic transducer in the axial direction and being positioned to reach the last piezoelectric layer of the ultrasonic transducer in the axial direction, and the second end extending toward the amplitude amplification element in the axial direction, the second end being positioned to reach a predetermined position beyond the flange in the axial direction.

21. The ultrasonic treatment apparatus according to claim 20, wherein the recess is formed on the outer surface of the inner casing.

22. An ultrasonic treatment apparatus for medical procedures on an object being treated, comprising:
 a transducer unit that includes an ultrasonic transducer generating ultrasonic vibration and having an axial end outputting the ultrasonic vibration therefrom, a flange attached to the ultrasonic transducer so as to extend from the axial end of the ultrasonic transducer in a radial direction of the ultrasonic transducer, and an amplitude amplification element coupled with the axial end of the ultrasonic transducer to receive the ultrasonic vibration generated by the ultrasonic transducer and to amplify an amplitude of the ultrasonic vibration, the amplitude amplification element having an axial tip end from which the amplified ultrasonic vibration is outputted;
 a probe having both an axial base-side end connectable with the axial tip end of the amplitude amplification element and an axial tip end at which a treatment portion is provided so that the amplified ultrasonic vibration is transmitted to the treatment portion;
 an inner casing that has an inner wall surface to provide an inner space and an outer circumferential surface, at least part of the amplitude amplification element, the flange, and the ultrasonic transducer being accommodated in the inner space along an axial direction of the inner casing, the flange being fixed to the inner wall surface; and
 an outer casing that has an inner circumferential surface to provide an inner space in which the inner casing is accommodated,
 wherein the outer circumferential surface of the inner casing and the inner circumferential surface of the outer casing air-tightly come in contact with each other; and
 the outer circumferential surface of the inner casing has a recess that has a ring-shaped section extending perpendicularly to the axial direction and extends in the axial direction such that the recess provides an air layer being charged air-tightly with air and blocking transmission of heat and vibration from the inner casing to the outer casing, the air layer having a length that covers both the flange and at least part of the ultrasonic transducer in the axial direction.

23. The ultrasonic treatment apparatus according to claim 22, wherein the inner and outer casings are substantially cylindrical.

24. The ultrasonic treatment apparatus according to claim 23, wherein the blocking layer is lower in heat conductivity than the inner and outer casings.

* * * * *